(12) United States Patent
Affaitati et al.

(10) Patent No.: US 8,980,197 B2
(45) Date of Patent: Mar. 17, 2015

(54) COLD STERILIZER

(75) Inventors: Pietro Affaitati, Albano Laziale Rm (IT); Andrea Fabbri, Pomezia Rm (IT)

(73) Assignee: IMS S.R.L., Pomezia, Rome (IT)

( * ) Notice: Subject to any disclaimer, the term of this patent is extended or adjusted under 35 U.S.C. 154(b) by 2025 days.

(21) Appl. No.: 11/988,161

(22) PCT Filed: Jul. 3, 2006

(86) PCT No.: PCT/IB2006/052224
§ 371 (c)(1),
(2), (4) Date: Mar. 19, 2008

(87) PCT Pub. No.: WO2007/007224
PCT Pub. Date: Jan. 18, 2007

(65) Prior Publication Data
US 2009/0104094 A1    Apr. 23, 2009

(30) Foreign Application Priority Data

Jul. 11, 2005  (IT) .............................. RM2005A0368

(51) Int. Cl.
*A61L 2/00*  (2006.01)
*A61L 2/18*  (2006.01)
*A61L 2/24*  (2006.01)

(52) U.S. Cl.
CPC ... *A61L 2/18* (2013.01); *A61L 2/24* (2013.01); *A61L 2202/24* (2013.01)
USPC ......................................................... 422/295

(58) Field of Classification Search
USPC ......................................................... 422/295
See application file for complete search history.

(56) References Cited

U.S. PATENT DOCUMENTS 4,402,407 A * 9/1983 Maly .............................. 206/438
5,225,160 A    7/1993 Sanford et al.

(Continued)

FOREIGN PATENT DOCUMENTS

WO           97/32610       9/1997
WO      2005/056060 A1      6/2005

OTHER PUBLICATIONS

International Search Report for PCT/IB2006/052224 mailed Dec. 18, 2006.

(Continued)

*Primary Examiner* — Kevin Joyner
(74) *Attorney, Agent, or Firm* — Nixon & Vanderhye P.C.

(57) ABSTRACT

A cold sterilizer, for deterging/decontaminating, sterilizing, drying and storing until the time of use medical devices, optionally the thermo-labile ones, in particular flexible and rigid endoscopes for surgical and diagnostic use, suitable for operating with sterilizing agents effective in the range 20-35° C., including the following parts in combination, a chamber, containing the tanks for deterging and sterilizing chemical agents, with closure means thereof; a room—which is or contains the container for flexible devices—equipped with optionally see-through closure means; a plurality of compartments substantially parallel thereamong and arranged substantially parallel to the side walls and to the support base, equipped with individual or common closure means and containing the casings in which the rigid devices are stored; means for the circulation of the above chemical agents among the tanks, the container, the casings and the medical devices contained therein; means for the automatic collection of the deterging and sterilizing chemical agents; means for assuring the circulation under pressure of said agents; means for detecting and controlling in real time the pressures exerted on the channels of the fluxed medical devices; means for allowing the purging of the channels of said medical devices; hydraulic and electrical connections; optionally, means for recording and printing the reprocessing data; optionally, means for facilitating the access to the mechanics thereof. FIG. 1 shows an embodiment of the cold sterilizer according to the invention.

14 Claims, 3 Drawing Sheets

(56) References Cited

U.S. PATENT DOCUMENTS

| | | | | |
|---|---|---|---|---|
| 5,858,305 | A * | 1/1999 | Malchesky | 422/28 |
| 6,585,934 | B1 * | 7/2003 | Oberleitner et al. | 422/28 |
| 6,585,943 | B1 * | 7/2003 | Sanford et al. | 422/307 |
| 7,316,249 | B2 * | 1/2008 | Cheong | 141/100 |
| 7,803,109 | B2 * | 9/2010 | Gomez | 600/121 |
| 2002/0163636 | A1 | 11/2002 | Oberleitner et al. | |
| 2004/0037736 | A1 * | 2/2004 | Perruchot et al. | 422/22 |
| 2005/0079094 | A1 * | 4/2005 | Mariotti et al. | 422/3 |

OTHER PUBLICATIONS

Written Opinion of the International Searching Authority, Jun. 29, 2007.

* cited by examiner

COLD STERILIZER

This application is the U.S. national phase of International Application No. PCT/IB2006/052224, filed 3 Jul. 2006, which designated the U.S. and claims priority to Italy Application No. RM2005A000368, filed 11 Jul. 2005, the entire contents of each of which are hereby incorporated by reference.

The present invention refers to the technical field of cold sterilization of medical devices in general, and in particular of rigid and flexible endoscopes for surgical and diagnostic use.

As it is known, the adoption of endoscopy technique and related endoscopes has become widespread in hospitals and nursing homes. It is also known that sterilizers should be capable of deterging/decontaminating, sterilizing, drying and storing until the time of use medical devices in general, and in particular rigid and flexible endoscopes.

In the current state of the art, less than satisfactory systems have been set up. In fact, the sterilizers adopted are complex under the designing standpoint or less than versatile, as not allowing the concomitant sterilization, e.g., of flexible endoscopes as well as of rigid ones in dedicated and separate compartments. Lastly, currently marketed sterilizers are not entirely reliable under the standpoint of the safety of those that have to manage their operation, owing to the hazardousness due to the manipulation of chemical agents.

For the sterilizing of, e.g., rigid and flexible endoscopes, there are mentioned by way of information the following apparatuses, which meet Standard UNI EN 14937 on sterilization: Steris system 1; steam autoclaves; plasma gas autoclaves; ethylene oxide autoclaves. These apparatuses however operate only at >50° C. temperatures, which are deemed harmful above all to flexible endoscopes.

The sole system allowing also, yet not concomitantly, the sterilization of rigid and flexible endoscopes at lower temperatures is the ERS-Cisa one. This system allows cold sterilization (20° C.-25° C.).

However, it has to be stressed that none of the mentioned apparatuses is capable of concomitantly reprocessing rigid and flexible endoscopes. Moreover, none of the apparatuses mentioned above and available on the market is capable of assuring complete safety for the management of the deterging/decontaminating and sterilizing chemical agents.

Therefore, in the field of sterilizing apparatuses for rigid endoscopes, flexible endoscopes and medical devices for surgical use, there is the need to overcome the above-mentioned drawbacks.

The cold sterilizer (i.e. a sterilizer suitable for operating with sterilizing agents effective in the range 20-35° C.) according to the invention allows to meet this need, further exhibiting other advantages that will be made evident hereinafter.

The cold sterilizer according to the invention for medical devices, optionally the thermo-labile ones, in particular for rigid and flexible endoscopes for surgical and diagnostic use, suitable for operating with sterilizing agents effective in the range 20-35° C., comprises the following parts in combination:

- a chamber, containing the tanks (1) for the deterging/decontaminating and sterilizing chemical agents, equipped with closure means (2);
- a room—which is or contains the container (3), either fixed and rigid or movable and soft, for flexible medical devices, the latter being provided with means for its sealing, opening, joining to and disjoining from the sterilizer—equipped with closure means (4);
- a plurality of compartments (5) substantially parallel thereamong and arranged substantially parallelly to the side walls and to the support base, equipped with individual or common closure means (6) and containing the casings (7), provided with means for their sealing, opening, joining to and disjoining from the sterilizer, in which the rigid medical devices (8) are stored;
- means for the circulation of the above chemical agents, among the tanks (1), the container (3), the casings (7) and the medical devices contained therein;
- means for the automatic and safe collection of the deterging/decontaminating and sterilizing chemical agents;
- means for assuring the circulation under pressure of said chemical agents;
- means for detecting and controlling in real time the pressures exerted on the channels of the fluxed medical devices;
- means for purging the channels of said medical devices;
- hydraulic and electrical connections;
- optionally, means for recording and printing the reprocessing data;
- optionally, means for facilitating the access to mechanics.

The closure means (2) of the chamber containing the tanks (1) may consist in a lid.

As already said, the container (3) may be fixed and rigid or movable and soft. In this latter case, it may provide a scavenging air valve and automatic connections with a check, in order to keep the reprocessed medical device sterile and for the inlet and outlet of the liquids. The movable container may be equipped with a liquid-tight zipper in order to allow its opening and the introduction of the flexible medical device under conditions of absolute isolation from the external environment.

The movable and soft container (3) can be made of a material selected from the group comprising silicone-based material, food silicone and food linen silicone and the closure means (4) of the room containing the container (3) for flexible medical devices may consist in a see-through lid, optionally polished.

Each of the casings (7) in which the rigid medical devices (8) are stored may have a substantially cylindrical or ovoid shape, and may optionally consist of two shells.

In each of the compartments (5), there may be provided reprocessing cycle start/stop means. In a variant, said means may consist in keys.

According to a preferred embodiment, the tanks (1) may consist in a single tank with a plurality of separated compartments, each containing a different chemical agent or a different component of the mixture to be used.

The means for the automatic collection of the deterging and sterilizing chemical agents may be in the form of a twin cap, a safety one and another one for collection, with a seal automatically pierceable during the operation of the sterilizer. The pierceable seal may be of aluminium.

In a variant of the invention, the means for circulating the deterging and sterilizing chemical agents may assure a pressure ranging from 150 to 500 mbar.

The means for detecting and controlling in real time the pressure exerted on the channels of the medical devices to be reprocessed may comprise a backlit liquid crystal display (LCD).

The means for purging the channels of the medical devices to be reprocessed may allow the flow of a sterile air stream.

The cold sterilizer of the present invention is particularly useful for cold sterilization with agents comprising peracetic acid and 5,7-diphenyl-1,3-diazoadamantan-6-one effective in the range 20-35° C.

In the cold sterilizer of the present invention, the tanks (1) can be a single tank with a plurality of separated compartments each containing a different chemical agent or a different component of the mixture to be used.

The cold sterilizer of the present invention in the embodiments providing three tanks (1) or three separated compartments of a single tank (1) can contain adazone, peracetic acid and proteazone respectively.

The cold sterilizer according to the present invention may find application in all medical specialties where it is necessary to sterilize medical devices in general, and in particular rigid and flexible endoscopes. Purely by way of non-exhaustive example, we will mention operating rooms, bronchoscopy, pneumatology, intensive care, endoscopy, Ear, Nose and Throat wards, etc.

So far, the present invention has been described only generally. With the aid of FIGS. 1, 2, 3 and of the example, hereinafter it will be given a more detailed description of specific embodiments thereof, aimed at making better understood the objects, features, advantages and application modes thereof.

EXAMPLE

It is exemplified a sterilizer according to the invention capable of concomitantly or asynchronously sterilizing three rigid endoscopes, with a maximum length of 50 cm, and one flexible endoscope.

The exemplified sterilizer has a length of 100 cm, a height of 45 cm, and a depth of 70 cm. Its weight is of about 70 kg. The utilized deterging and sterilizing chemical liquids are contained in a tank with three compartments, containing adazone, peracetic acid and proteazone, respectively.

Adazone is 5,7-diphenyl-1,3-diazoadamantan-6-one, while proteazone consists of 0.25 g of adazone, 25 g of a plurienzymatic mixture (amylase, lipase, protease and carbohydrates) with a germicide surfactant complex having a linear structure (R=C10-C14), 0.07 g of DTPA, optionally other components, and 100 cm$^3$ of water.

With reference to the figures, into a chamber, obtained in the left side of the sterilizer and equipped with the related closure lid (2), it is located the tank (1) for the deterging and sterilizing chemical agents.

Figure 3:
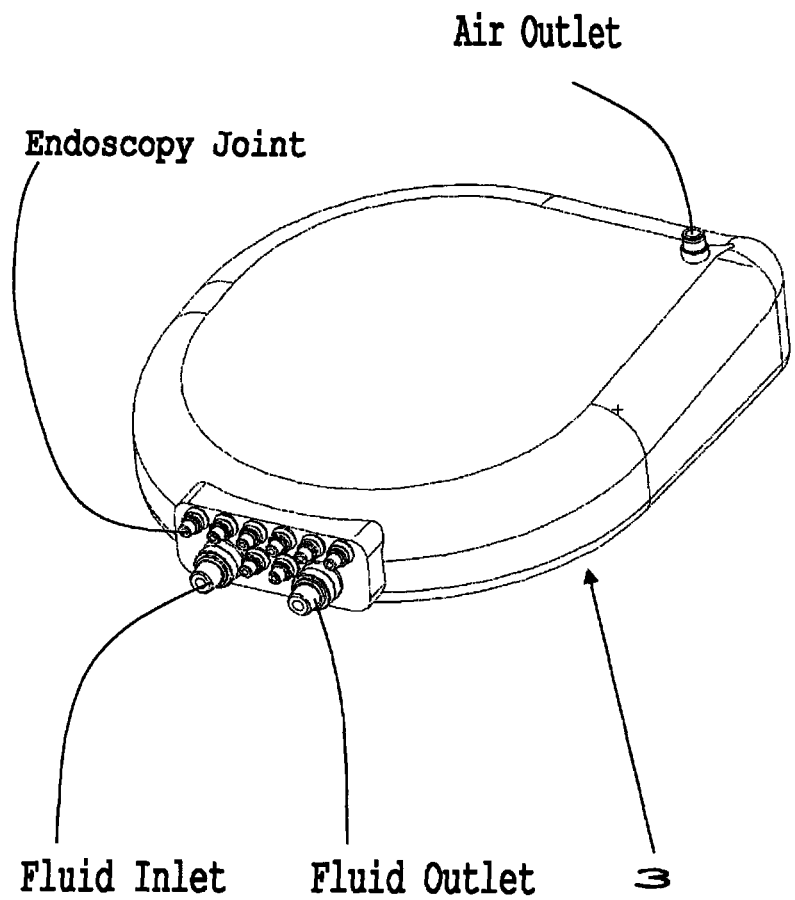
FIG. 3 shows very schematically an enlarged perspective view of the container (3) of FIG. 1.

At the center of the top portion of the sterilizer, it is located the container (3), made in blue food-linen-silicone for containing the flexible endoscopes, with the polished see-through closure lid (4) thereof. Inside of the container (3), as it is more clearly shown in FIG. 3, there are located eight joints for the related connections to the flexible endoscopes to be treated, and it is possible to perform a tightness test. After having filled the container (3), the chemical liquids cross the eight endoscopy joints and reach the flexible endoscopes, so deterging and sterilizing them.

Figure 2:
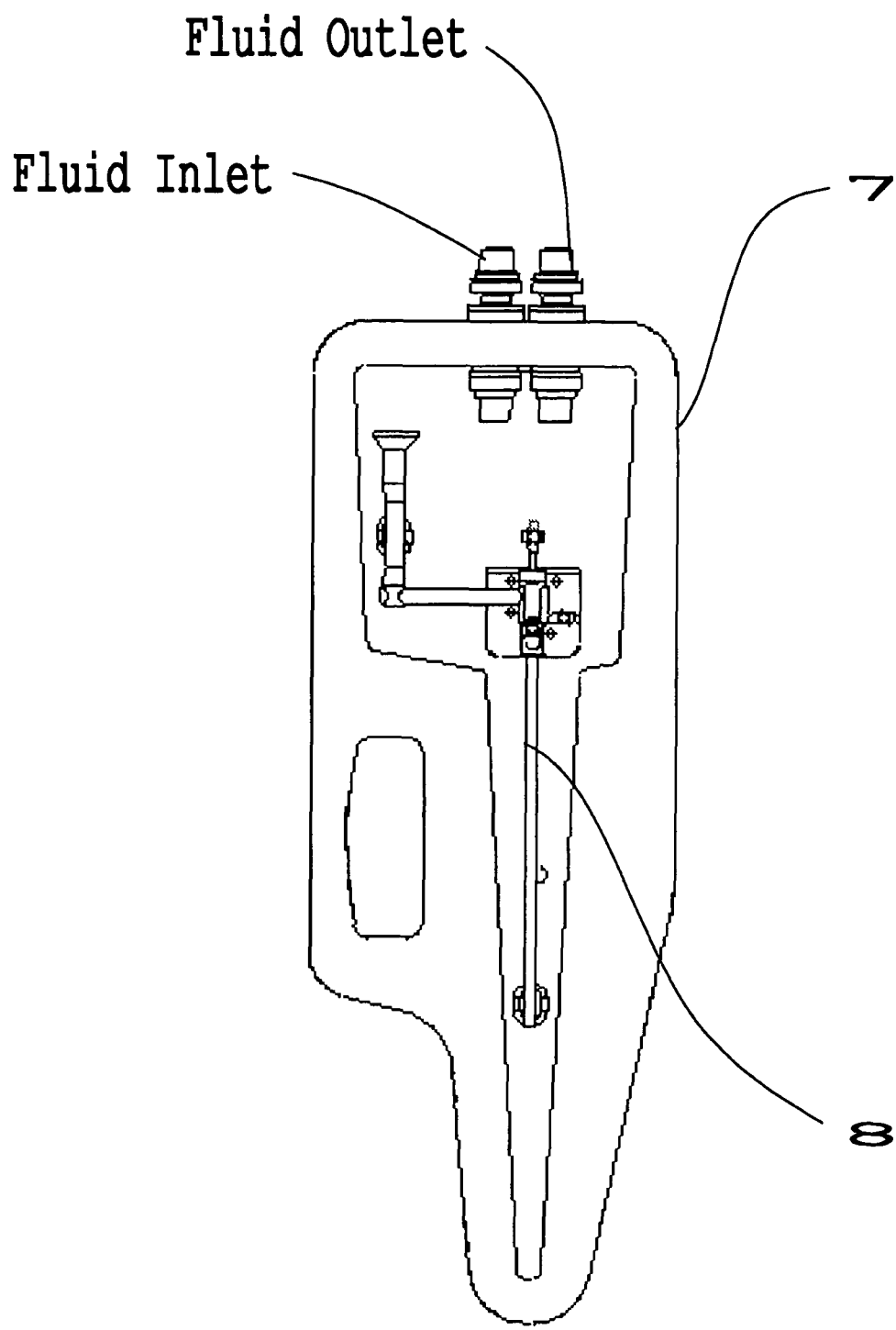
FIG. 2 shows a side view of an embodiment of a casing (7) according to the invention containing a rigid endoscope to be processed in the sterilizer.

Always at the center of the sterilizer, at the bottom thereof, there are located also three compartments (5), equipped with a common closure (6), for the reprocessing of the rigid endoscopes (8) contained in the suitable casings (7) (see in particular FIG. 2).

These casings are capable of containing all types of rigid endoscopes and medical devices, up to a maximum length of 50 cm.

On the right side of the sterilizer, there are located the 4-inch backlit LCD, the printer for reporting the process, the cycle start-stop keys (two for each reprocessing station) and the access to the electronic cards of the machine.

Figure 1:
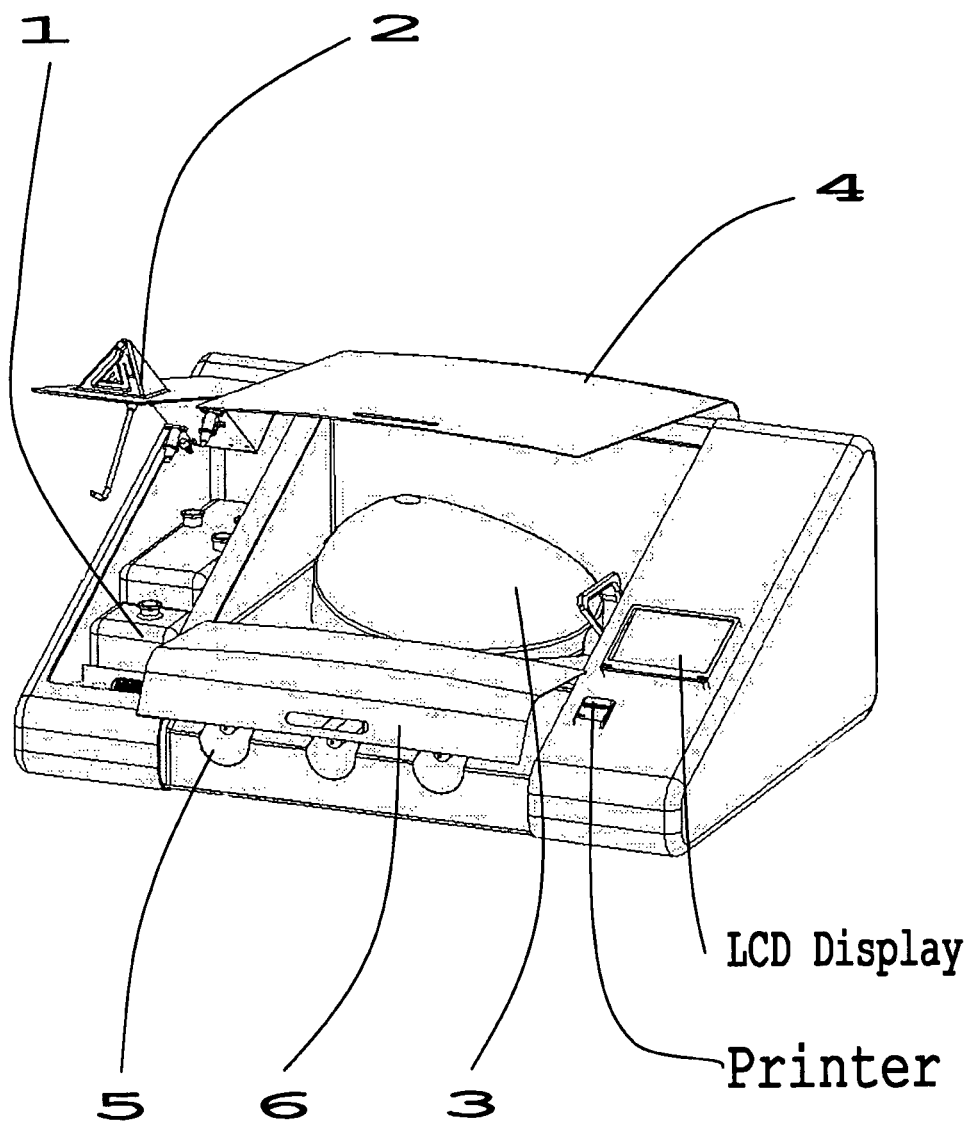
FIG. 1 is a perspective view of an embodiment of the cold sterilizer of the present invention.

On the back of the sterilizer, not shown in FIG. 1, there are the hydraulic connections for the sterilizer operation and the removable panel for accessing to the mechanics thereof.

The invention claimed is:

1. A cold sterilizer for medical devices suitable for operating with sterilizing agents effective in the range 20-35° C., comprising:
   a chamber, containing tanks housing deterging/decontaminating and sterilizing chemical agents, the chamber having a closure;
   a room including a container housing a flexible medical device, the container being sealable and including connections for the sterilizing chemical agents, the room having a closure;
   a plurality of compartments substantially parallel thereamong and arranged substantially parallel to side walls and to a support base of the room, the compartments being equipped with a closure and containing casings in which rigid medical devices are stored, the casing being sealable and including connections for the sterilizing chemical agents;
   a collecting area that collects the deterging and sterilizing chemical agents;
   hydraulic connections effecting circulation and purging of the sterilizing chemical agents under pressure, among the tanks, the container, the medical devices and channels thereof;
   a printing unit for recording and printing the reprocessing data; and
   a display unit that detects and controls in real time the pressures exerted on the channels of the medical devices,
   wherein the cold sterilizer is sized and configured to be portable.

2. The sterilizer according to claim 1, wherein the closure of the chamber containing the tanks comprises a lid.

3. The cold sterilizer according to claim 1, wherein the container housing the flexible medical device is movable and soft, and wherein the container is made of a material selected from the group comprising substantially silicone-based material, food silicone and food linen silicone, and wherein the closure of the room containing the container comprises a see-through lid.

4. The cold sterilizer according to claim 1, wherein each of the plurality of compartments has a substantially cylindrical shape.

5. The cold sterilizer according to claim 1, wherein each of the casings of the rigid medical devices has a substantially cylindrical or ovoid shape.

6. The cold sterilizer according to claim 1, wherein for each of the plurality of compartments there is provided reprocessing cycle start/stop mechanism.

7. The cold sterilizer according to claim 6, wherein the reprocessing cycle start/stop mechanism is keys.

8. The cold sterilizer according to claim 1, wherein the collecting area comprises a twin cap, one of which is a safety cap for collection, with a seal automatically pierceable during operation of the sterilizer.

9. The sterilizer according to claim 8, wherein the pierceable seal is of aluminium.

10. The cold sterilizer according to claim 1, wherein the hydraulic connections circulating the chemical agents assures a pressure ranging from 150 to 500 mbar.

11. The cold sterilizer according to claim 1, wherein the display unit comprises a backlit liquid crystal display.

12. The cold sterilizer according to claim 1, wherein the hydraulic connections allow the flow of a sterile air stream.

13. The cold sterilizer according to claim 1, wherein the tanks comprise a single tank with a plurality of separated compartments each containing a different chemical agent or a different component of a mixture to be used.

14. The cold sterilizer according to claim 1, comprising three tanks or three separated compartments of a single tank containing adazone, peracetic acid and proteazone respectively.

* * * * *